United States Patent
Satpathy

(10) Patent No.: US 10,955,406 B2
(45) Date of Patent: Mar. 23, 2021

(54) DIFFUSE OPTICAL IMAGING WITH MULTIPLE BEAMS

(71) Applicant: Open Water Internet Inc., San Francisco, CA (US)

(72) Inventor: Sarmishtha Satpathy, San Francisco, CA (US)

(73) Assignee: Open Water Internet Inc., San Francisco, CA (US)

( * ) Notice: Subject to any disclaimer, the term of this patent is extended or adjusted under 35 U.S.C. 154(b) by 53 days.

(21) Appl. No.: 16/267,957

(22) Filed: Feb. 5, 2019

(65) Prior Publication Data

US 2020/0249154 A1    Aug. 6, 2020

(51) Int. Cl.
*G01N 33/49* (2006.01)
*G01N 21/3577* (2014.01)
*G01N 21/45* (2006.01)
*G01N 21/47* (2006.01)

(52) U.S. Cl.
CPC ..... *G01N 33/4925* (2013.01); *G01N 21/3577* (2013.01); *G01N 21/45* (2013.01); *G01N 21/4795* (2013.01); *G01N 2021/451* (2013.01)

(58) Field of Classification Search
CPC .......... G01N 21/49; G01N 2021/1706; G01N 21/1702; G01N 21/1717; G01B 9/02003; G01B 9/02017; G01B 9/02024; G01B 9/02029; G01B 9/02084
See application file for complete search history.

(56) References Cited

U.S. PATENT DOCUMENTS

| | | |
|---|---|---|
| 6,172,760 B1 | 1/2001 | Son |
| 6,956,650 B2 | 10/2005 | Boas |
| 7,119,906 B2 | 10/2006 | Pepper |
| 7,460,248 B2 | 12/2008 | Kurtz |
| 7,551,809 B2 | 6/2009 | Taira |
| 7,610,082 B2 | 10/2009 | Chance |
| 7,647,091 B2 | 1/2010 | Ntziachristos |
| 7,728,986 B2 | 6/2010 | Lasker |
| 7,804,070 B1 | 9/2010 | Pan |
| 7,821,640 B2 | 10/2010 | Koenig |
| 7,822,468 B2 | 10/2010 | Stammes |
| 7,826,878 B2 | 11/2010 | Alfano |
| 7,898,649 B2 | 3/2011 | Masumura |

(Continued)

OTHER PUBLICATIONS

Arridge et al. Nonuniqueness in diffusion-based optical tomography, Optics Letters, Jun. 1, 1998, vol. 23, No. 11, pp. 882-884.
(Continued)

*Primary Examiner* — Michael P LaPage
(74) *Attorney, Agent, or Firm* — Freestone Intellectual Property Law PLLC; Aaron J. Visbeek

(57) ABSTRACT

A first wavelength-shifted exit signal is interfered with a first reference beam and a second wavelength-shifted exit signal is interfered with a second reference beam. The first wavelength-shifted exit signal and the second wavelength-shifted exit signal have different wavelengths. A first and second interference pattern are captured by an image sensor in a single image capture. The first reference beam is incident on the image sensor at a first reference angle and the second reference beam is incident on the image sensor at a second reference angle different from the first reference angle.

15 Claims, 11 Drawing Sheets

(56) References Cited

U.S. PATENT DOCUMENTS

| | | |
|---|---|---|
| 7,965,389 B2 | 6/2011 | Da Silva |
| 7,983,740 B2 | 7/2011 | Culver |
| 7,928,896 B2 | 8/2011 | Jin |
| 8,014,847 B2 | 9/2011 | Shastri |
| 8,120,784 B2 | 2/2012 | Da Silva |
| 8,170,651 B2 | 5/2012 | Lorenzo |
| 8,239,006 B2 | 8/2012 | Zhu |
| 8,263,947 B2 | 9/2012 | Da Silva |
| 8,289,502 B2 | 10/2012 | Yoshida |
| 8,326,567 B2 | 12/2012 | Masumura |
| 8,330,642 B2 | 12/2012 | Jin |
| 8,355,131 B2 | 1/2013 | Bakker |
| 8,357,915 B2 | 1/2013 | Guyon |
| 8,374,409 B2 | 2/2013 | Jochemsen |
| 8,416,421 B2 | 4/2013 | Wang |
| 8,450,674 B2 | 5/2013 | Yang |
| 8,451,450 B2 | 5/2013 | Heng |
| 8,520,921 B2 | 8/2013 | Ziegler |
| 8,525,998 B2 | 9/2013 | Yaqoob |
| 8,527,242 B2 | 9/2013 | Granot |
| 8,531,662 B2 | 9/2013 | Van Der Mark |
| 8,563,932 B2 | 10/2013 | Fang |
| 8,634,077 B2 | 1/2014 | Hu |
| 8,649,015 B2 | 2/2014 | Ichihara |
| 8,917,442 B2 | 3/2014 | Baym |
| 8,717,574 B2 | 5/2014 | Yang |
| 8,792,102 B2 * | 7/2014 | Patil .................... G01J 3/4531 356/456 |
| 8,814,795 B2 | 8/2014 | Derode |
| 8,817,255 B2 | 8/2014 | Masumura |
| 8,830,573 B2 | 9/2014 | Cui |
| 8,847,175 B2 | 9/2014 | Laidevant |
| 8,937,284 B2 | 1/2015 | Fang |
| 8,954,130 B2 | 2/2015 | Masumura |
| 8,976,433 B2 | 3/2015 | Masumura |
| 9,012,869 B2 | 4/2015 | Andersson-Engels |
| 9,036,970 B2 | 5/2015 | Guyon |
| 9,037,216 B2 | 5/2015 | Hielscher |
| 9,057,695 B2 | 6/2015 | Masumura |
| 9,131,851 B2 | 9/2015 | Fukutani |
| 9,134,229 B2 | 9/2015 | Lesage |
| 9,179,842 B2 | 11/2015 | Nakaji |
| 9,207,171 B2 | 12/2015 | Nadakuditi |
| 9,234,841 B2 | 1/2016 | Wang |
| 9,282,932 B2 | 3/2016 | Kudo |
| 9,297,752 B2 | 3/2016 | Shimokawa |
| 9,304,490 B2 | 4/2016 | Masumura |
| 9,313,423 B2 | 4/2016 | Wang |
| 9,335,604 B2 | 5/2016 | Popovich |
| 9,335,605 B2 | 5/2016 | Wang |
| 9,341,569 B2 | 5/2016 | 'T Hooft |
| 9,354,166 B2 | 5/2016 | Judkewitz |
| 9,373,020 B2 | 6/2016 | Kudo |
| 9,407,796 B2 | 8/2016 | Dinten |
| 9,427,213 B2 | 8/2016 | Suzuki |
| 9,480,425 B2 | 11/2016 | Culver |
| 9,486,142 B2 | 11/2016 | Hielscher |
| 9,488,574 B2 | 11/2016 | Koehler |
| 9,509,956 B2 | 11/2016 | Piestun |
| 9,622,663 B2 | 4/2017 | Fang |
| 9,689,797 B2 | 6/2017 | Sun |
| 9,724,489 B2 | 8/2017 | Barbour |
| 9,730,649 B1 | 8/2017 | Jepsen |
| 9,750,413 B2 | 9/2017 | Sandusky |
| 2010/0016732 A1 | 1/2010 | Wells |
| 2012/0070817 A1 | 3/2012 | Yang |
| 2013/0276542 A1 * | 10/2013 | Herzog ................ A61B 5/0073 73/655 |
| 2014/0081096 A1 | 3/2014 | Baym |
| 2014/0114181 A1 | 4/2014 | Wu |
| 2014/0303473 A1 | 10/2014 | Nanaumi |
| 2015/0182121 A1 | 7/2015 | Barbour |
| 2015/0238092 A1 | 8/2015 | Masumura |
| 2015/0241342 A1 | 8/2015 | Zhou |
| 2015/0346027 A1 | 12/2015 | Khare |
| 2015/0351635 A1 | 12/2015 | Cerussi |
| 2016/0085135 A1 | 3/2016 | Park |
| 2016/0157723 A1 | 6/2016 | Kanick |
| 2016/0262723 A1 | 9/2016 | Zhu |
| 2016/0363527 A1 | 12/2016 | Ruan |
| 2017/0118423 A1 | 4/2017 | Zhou |
| 2017/0156600 A1 * | 6/2017 | Ntziachristos ......... A61B 5/441 |
| 2017/0163946 A1 | 6/2017 | Komanduri |
| 2017/0168565 A1 | 6/2017 | Cohen |
| 2017/0202633 A1 | 7/2017 | Liu |
| 2017/0230555 A1 | 8/2017 | Tabirian |
| 2017/0231501 A1 | 8/2017 | Culver |
| 2019/0083059 A1 * | 3/2019 | Byrnes ..................... A61B 8/15 |

OTHER PUBLICATIONS

Hofmann et al. Differential light detector, Rev. Sci. Instrum, Feb. 1979, vol. 50, No. 2, pp. 249-252.

Freund et al. Memory Effects in Propagation of Ooptical Waves through Disordered Media, Physical Review Letters, Nov. 14, 1988, vol. 61, No. 20, pp. 2328-2331.

Goodman et al. Wavefront-Reconstruction Imaging Through Random Media, Jun. 15, 1966, vol. 8, No. 12, pp. 311-313.

Peng et al. Low loss liquid crystals for infrared applications, Liquid Crystal, 2014, vol. 41, No. 11, pp. 1545-1552.

* cited by examiner

DIFFUSE OPTICAL IMAGING WITH MULTIPLE BEAMS

TECHNICAL FIELD

This application is related to optical imaging and in particular to optical imaging with multiple beams.

BACKGROUND INFORMATION

Imaging devices are used in contexts such as healthcare, navigation, and security, among others. Imaging systems often measure radio waves or light waves to facilitate imaging. Imaging that measures light scattered by an object is especially challenging and advances to the devices, systems, and methods to improve optical imaging are sought to increase speed, increase resolution, reduce size and/or reduce cost.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

DETAILED DESCRIPTION

Figure 1A:
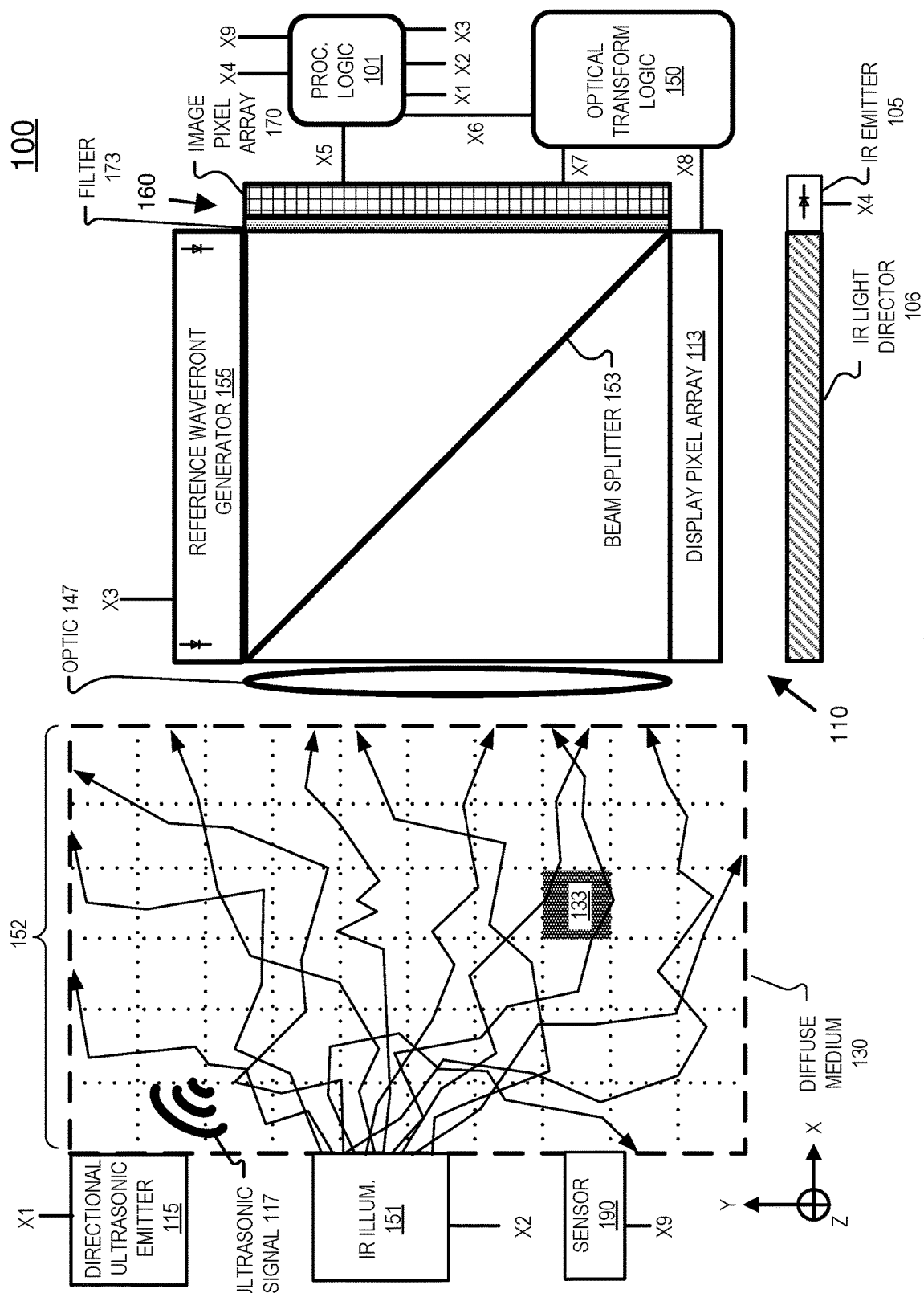
FIGS. 1A-1C illustrate an example imaging system that includes a display pixel array, an image pixel array, and a beam splitter, in accordance with an embodiment of the disclosure.

Embodiments of a system, device, and method for multiple beam imaging are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

This disclosure will generally describe imaging a diffuse medium in the context of human tissue in the medical context, however, the content of this disclosure may be applied to medical imaging, navigation, security, scientific research, or other contexts that image diffuse mediums or objects.

Human tissue is translucent to infrared light and to at least some wavelengths of visible light, although different parts of the human body (e.g. skin, blood, bone) exhibit different absorption coefficients. Researchers have attempted to use the properties of infrared light for medical imaging purposes, but size and cost constraints have been prohibitive for wide-scale adoption. Illuminating tissue and other diffuse mediums with visible light and near-infrared light for imaging purposes is sometimes referred to as Diffuse Optical Tomography. In one Diffuse Optical Tomography technique, time-of-flight (TOF) imaging can theoretically be employed by measuring the time it takes for "ballistic" photons (those photons that are not scattered) to pass through tissue. Since the ballistic photons reach the sensor the fastest, they are the least scattered (have the shortest optical path) and thus some conclusion can be drawn to create an image of the tissue that is illuminated by infrared light. However, TOF imaging generally requires specialty hardware (e.g. picosecond pulsed lasers and single photon detectors) to facilitate ultra-fast shutters on sensors that are able to image at the speed of light and the systems are overall very expensive and bulky. TOF imaging also requires an input of approximately 10-100 fold (or more) light intensity into the body than is received at the detector. Thus, efficacy and power limitations as well as safety limits on input intensity limit TOF imaging resolution, depth and utility.

In contrast to TOF imaging, some embodiments may illuminate a diffuse medium with an infrared light or visible light while an ultrasound emitter is focused on a particular voxel. In a dual-beam imaging system of the disclosure, a first illuminator emitting a first illumination beam having a first wavelength (e.g. 600 nm) and a second illuminator emitting a second illumination beam having a second wavelength (e.g. 800 nm) may illuminate a diffuse medium while an ultrasound emitter is focused on a particular voxel. The first illumination beam and the second illumination beam encountering the particular voxel may be wavelength-shifted by the ultrasonic signal into a first wavelength-shifted exit signal and a second wavelength-shifted exit signal, respectively. The first wavelength-shifted exit signal is the portion of the first illumination beam that is reflected from and/or transmitted through the voxel (while the ultrasonic emitter is focused on the voxel). The second wavelength-shifted exit signal is the portion of the second illumination beam that is reflected from and/or transmitted through the voxel (while the ultrasonic emitter is focused on the voxel). The first wavelength-shifted exit signal is interfered with a first reference beam to generate a first interference pattern on the image sensor and the second wavelength-shifted exit signal is interfered with a second reference beam to generate a second interference pattern on the image sensor. The first reference beam is received by the image sensor at a first reference angle and the second reference beam is received by the image sensor at a second reference angle that is different than the first reference angle. The image sensor may capture the first interference pattern and the second interference pattern in a single image capture.

A frequency domain image may be generated using a Fourier transform operation on the image. A first portion of the frequency domain image associated with the first interference pattern may be compared to a second portion of the frequency domain image associated with the second interference pattern. Notably, since the first reference beam and the second reference beam were incident at different angles, the first interference pattern and the second interference pattern are in different portions of the frequency domain image. A first intensity associated with the first interference pattern may be compared with a second intensity associated with the second interference pattern to generate a difference value. The difference value may be representative of the absorption level of a particular voxel to the first wavelength and second wavelength.

When embodiments of the disclosure are used to image tissue, the difference value may be representative of the oxygenation or deoxygenation of blood in tissue. Since Hemoglobin found in red blood cells has different absorption properties depending on the oxygenated or deoxygenated blood, the difference value may be representative of the oxygen state of the blood flowing through a particular voxel. The capability to capture both the first interference pattern and the second interference pattern simultaneously (in a single image), assists in increasing the scanning speed. Additionally, simultaneous dual-beam image capture increases measurement accuracy since the different illumination beams are not separated by time and thus movement of the tissue between measurements is reduced, if not eliminated. By capturing images of the exit signal changes at a voxel or group of voxels (e.g. oxygen saturation in red blood cells, scattering changes induced by potential differences in an activated neuron, fluorescent contrast agents and other optical changes) in the diffuse medium, changes to that voxel or group of voxels can be recorded over time. Extraction logic may isolate the interference patterns from the dual wavelength-shifted exit signals, extract intensity data and then populate a voxel value of a composite image with a difference value derived from the intensity data. The composite image may include a three-dimensional image of the diffuse medium. These embodiments and others will be described in more detail with references to FIGS. 1A-6.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Throughout this specification, several terms of art are used. These terms are to take on their ordinary meaning in the art from which they come, unless specifically defined herein or the context of their use would clearly suggest otherwise. For the purposes of the disclosure, visible light has a wavelength from approximately 400 nm to 700 nm and near-infrared light has a wavelength from approximately 700 nm to 2500 nm.

Figure 1B:
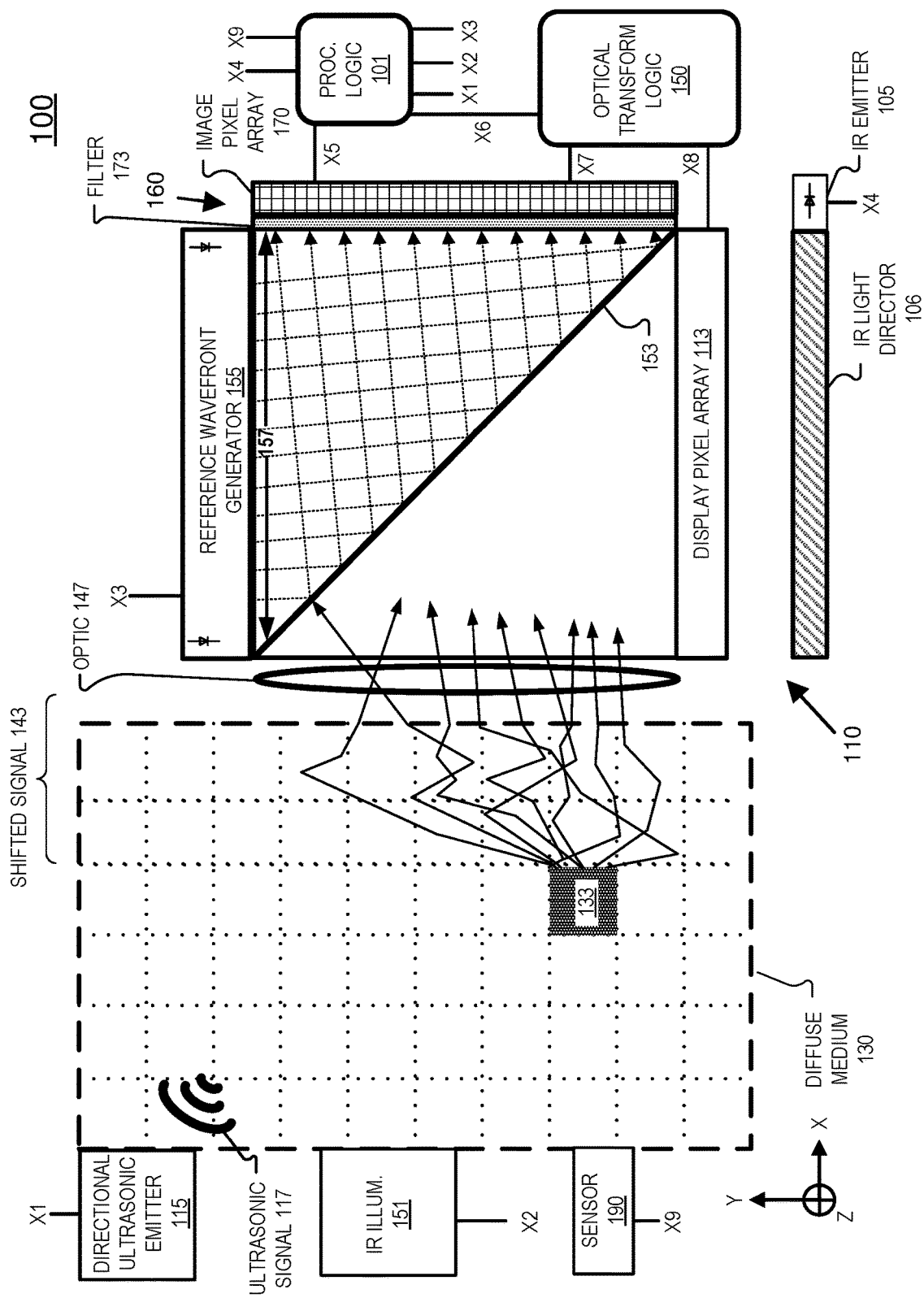
Figure 1C:
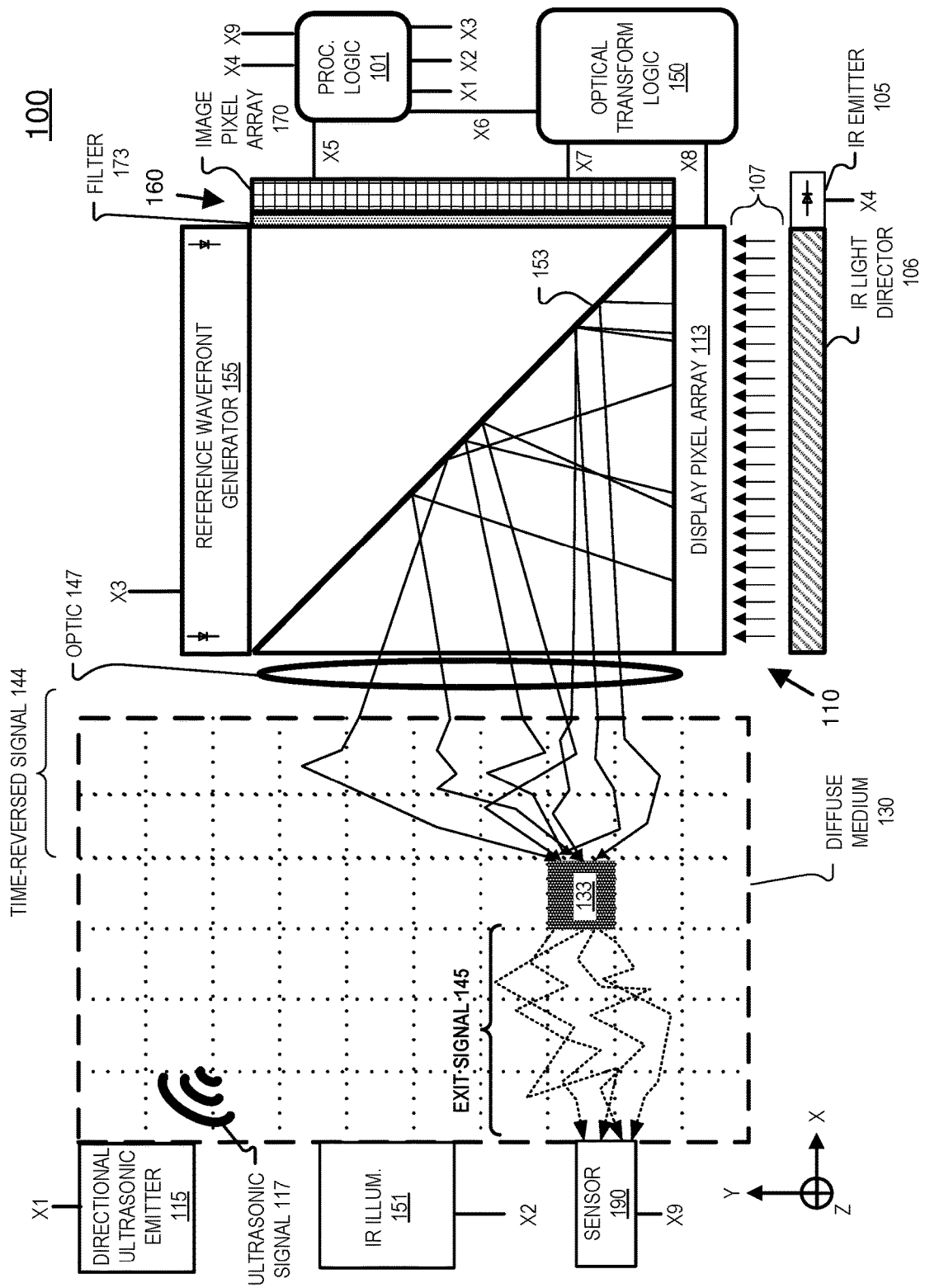

FIGS. 1A-1C illustrate an example imaging system that includes a display pixel array, an image pixel array, and a beam splitter, in accordance with an embodiment of the disclosure. In FIG. 1A, imaging system 100 includes processing logic 101, a spatial light modulator (SLM) 110, and image module 160. Imaging module 160 includes image pixel array 170 and filter(s) 173. In FIG. 1A, imaging system 100 also includes a directional ultrasonic emitter 115 coupled to be driven by processing logic 101. In FIG. 1A, SLM 110 includes an infrared emitter 105, an infrared light director 106, and a display pixel array 113. Display pixel array 113 may be an LCD (liquid crystal display), for example. The LCD display may be an active-matrix (using thin-film-transistors) or a passive matrix LCD. In one embodiment, the LCD display has pixels that are smaller than 7 microns. In other embodiments, SLM 110 may include a reflective architecture such as a liquid-crystal-on silicon (LCOS) display being illuminated by infrared light, for example. Other known transmissive and reflective display technologies may also be utilized as SLM 110. System 100 may include a plurality of discrete devices that incorporate components of system 100, in some embodiments.

Processing logic 101 may include a processor, microprocessor, cluster of processing cores, FPGA (field programmable gate array), and/or other suitable combination of logic hardware. In some embodiments, memories (not illustrated) are integrated into the processing logic to store instructions to execute operations and/or store data. An external memory or memories (not illustrated) may also be coupled to processing logic 101 to store instructions to execute operations and/or store data. A "memory" or "memories" described in this disclosure may include volatile or non-volatile memory architectures.

System 100 includes an infrared illuminator 151. Processing logic 101 is coupled to selectively activate IR illuminator 151 via output X2, in the illustrated embodiment. Infrared illuminator 151 may include an infrared laser generating a general illumination emission 152. Of course, an infrared laser may generate monochromatic coherent infrared light. Monochromatic light may be defined as light within a 4 nm frequency band, for example. The infrared light that IR illuminator 151 emits may be centered around a frequency in the 680-1000 nm range. In one embodiment, the infrared light that IR illuminator 151 emits may be centered around a frequency in the 1600-1700 nm range. In one example, IR illuminator 151 generates monochromatic light centered around 680 nm. In one example, IR illuminator 151 generates monochromatic light centered around 850 nm. The infrared illuminator 151 is disposed to direct the general illumination emission 152 into the diffuse medium 130. In the context of tissue, general illumination emission 152 will be significantly scattered within tissue within as little as 1 cm of depth into the tissue when tissue is the diffuse medium 130. At least a portion of the general illumination emission 152 will encounter voxel 133, as illustrated in FIG. 1A.

System 100 also includes an ultrasonic emitter 115. Ultrasonic emitter 115 is configured to focus an ultrasonic signal 117 to a point in three-dimensional space. In the medical context, the ultrasonic emitter 115 is configured to focus an ultrasonic signal 117 to a voxel within the human body. The voxel may be within the brain, abdomen, or uterus, for example. Processing logic 101 is coupled to drive directional ultrasonic emitter 115 to focus ultrasonic signal 117 to different locations in three-dimensional space via output X1, in the illustrated embodiment. The directional ultrasonic emitter 115 can be driven to focus an ultrasonic signal to voxel 133 in three-dimensional diffuse medium 130, for example. Focusing an ultrasonic signal 117 to a given voxel of tissue (e.g. voxel 133) influences the portion of illumination emission 152 that encounters the voxel by wavelength-shifting that portion of illumination emission 152 that propagates through that voxel.

In FIG. 1B, the wavelength-shifted portion of the general illumination emission 152 is illustrated as shifted infrared imaging signal 143. Being influenced by ultrasonic signal 117, shifted signal 143 has a different wavelength (hereinafter referred to as lambda-two) than general illumination emission 152 (referred to as lambda-one). In some embodiments, the delta between lambda-one and lambda-two may be less than 1 nanometer. In an embodiment, the delta between lambda-one and lambda-two may be less than 20 femtometer.

System 100 receives (at least a portion of) shifted infrared imaging signal 143. An input optic 147 may optionally be included in system 100. Input optic 147 may receive shifted signal 143 and direct the shifted signal 143 to be incident on image pixel array 170. In one embodiment, input optic 147 is configured to filter out an angled portion of the shifted signal 143. In one embodiment, the angled portion of the shifted signal 143 has a plus-or-minus angle of incidence upon the input optic 147 that is higher than an angle threshold. In one embodiment, the sine of twice the angle threshold is approximately equivalent to a wavelength of the shifted signal 143 (lambda-two) divided by twice a distance between two pixels of the image pixel array 170. In one embodiment, the angle threshold is between five and seven degrees.

Still referring to FIG. 1B, reference wavefront generator 155 generates an infrared reference wavefront 157 having the lambda-two wavelength so that infrared reference wavefront 157 interferes with the incoming shifted signal 143. Reference wavefront generator 155 may include one or more laser diodes and corresponding optics to generate a substantially uniform wavefront. Processing logic 101 is coupled to selectively activate reference wavefront generator 155 via output X3, in the illustrated embodiment.

A first portion of the infrared reference wavefront 157 is redirected to the image pixel array 170 by beam splitter 153 while a second remaining portion of wavefront 157 passes through beam splitter 153. Shifted signal 143 encounters beam splitter 153 and a first portion of the shifted signal 143 passes through beam splitter 153 while the remaining second portion of the shifted signal 143 is reflected by beam splitter 153. The first portion of the shifted signal 143 that passes through beam splitter 153 interferes with the first portion of wavefront 157 that is redirected to image pixel array 170 and image pixel array 170 captures an infrared image of the interference between shifted signal 143 and infrared reference wavefront 157.

In one embodiment, reference wavefront generator 155 is disposed to deliver the infrared reference wavefront 157 to the image pixel array 170 at an angle to a pixel plane of the image pixel array 170. Image pixel array 170 may include image pixels disposed in a two-dimensional rows and columns that define the pixel plane of the image pixel array 170. In one embodiment, the angle is between five and seven degrees so that the infrared reference wavefront 157 encounters the image pixels of image pixel array 170 at a non-orthogonal angle. Angling the infrared reference wavefront 157 may change the interference orientation and size between shifted signal 143 and wavefront 157, which may enable better signal isolation at the image pixel array 170. Processing logic 101 is coupled to initiate the image capture by image pixel array 170 via output X5, in the illustrated embodiment.

A linear polarizer may be included in system 100 to polarize shifted signal 143 to have the same polarization orientation as infrared reference wavefront 157. The light source of reference wavefront generator 155 may generate linear polarized light which imparts a polarization orientation to infrared reference wavefront 157. The linear polarizer may be included in optic 147, filter 173, or in a linear polarizer disposed between optic 147 and filter 173.

In the illustrated embodiment, an infrared filter 173 is disposed between beam splitter 153 and image pixel array 170. Infrared filter 173 may pass the wavelength of infrared light emitted by reference wavefront generator 155 (lamda-two) and reject ambient light.

Image pixel array 170 may be implemented with an a-Si (amorphous Silicon) thin film transistors, in some embodiments or a CMOS (Complimentary Metal-Oxide-Semiconductor) image sensor, in some embodiments. Image pixel array 170 can be a commercially available image sensor. In one embodiment, image pixel array 170 has image pixels having a pixel pitch of 3.45 microns. In one embodiment, image pixel array 170 has image pixels having a pixel pitch of 1.67 microns. The pixel resolution of image pixel array 170 may vary depending on the application. In one embodiment, the image pixel array 170 is 1920 pixels by 1080 pixels. In one embodiment, the image pixel array is 40 Megapixels or more. Image pixel array 170 can capture an infrared image of an interference between shifted signal 143 and IR reference wavefront 157 by measuring the image charge generated in each pixel during a given integration period that is determined by an electronic shutter. The electronic shutter may be a global shutter (where each pixel measures the incident light during a same time period) or a rolling shutter. The electronic shutter can be actuated by processing logic 101 via input/output X5. Input/output X5 may include digital input/output lines as well as a data bus. Image pixel array 170 is communicatively coupled to optical transform logic 150 to send the captured infrared image(s) to optical transform logic 150 for further processing. In some embodiments, the integration period of the pixels of the image pixel array 170 is determined by the length of a laser pulse. Image pixel array 170 may include a local (on-board) digital signal processor (DSP), in some embodiments, and optical transform logic 150 may receive the captured infrared images from the DSP.

Optical transform logic 150 is coupled to image pixel array 170 via communication channel X7, in the illustrated embodiment. Optical transform logic is also communicatively coupled to processing logic 101 via communication channel X6. Optical transform logic 150 is coupled to receive the captured infrared image from the image pixel array and provide a holographic pattern to be driven onto the display pixel array 113. The optical transform logic 150 is configured to extract phase data of the interference captured by the infrared image and the holographic pattern is generated from the phase data. A more detailed description of example optical transform logic is described in U.S. patent application Ser. No. 15/942,480, which is hereby incorporated by reference.

Referring now to FIG. 1C, display pixel array 113 is configured to generate an infrared holographic imaging signal 144 (reconstruction of signal 143) according to a holographic pattern driven onto the array 113. Optical transform logic 150 is coupled to provide the array 113 the holographic pattern via communication channel X8.

In FIG. 1C, display pixel array 113 is illustrated as a transmissive LCD that is illuminated by infrared wavefront 107. In the illustrated embodiment, infrared (IR) emitter 105 is coupled to be driven by output X4 of processing logic 101. When processing logic 101 turns on (activates) IR emitter 105, infrared light propagates into IR light director 106. IR light director 106 may be a light guide plate similar to those found in conventional edge lit LCDs. IR light director 106 may be a slim prism utilizing TIR (total internal reflection). IR light director 106 redirects the infrared light toward display pixel array 113. IR light director 106 may include a sawtooth grating to redirect the infrared light toward array 113. IR emitter 105 is an infrared laser diode that emits monochromatic infrared light, in one embodiment.

Steerable infrared beams can be generated by SLM 110 by driving different holographic patterns onto display pixel array 113. Each different holographic pattern can steer (focus) the infrared light in a different direction. The directional nature of the infrared beam is influenced by the constructive and destructive interference of the infrared light emitted from the pixels of SLM 110. As an example, a holographic pattern that includes different "slits" at different locations can generate different infrared beams. The "slits" can be generated by driving all the pixels in the display pixel array 113 to "black" (not transmissive) except for the pixels where the "slits" are located are driven to be "white" (transmissive) to let the infrared light propagate through. The pixel size of display pixel array 113 may be 1 micron, although in some embodiments pixels sized up to 10 times the wavelength of the infrared light can be used. In one example, if IR emitter 105 is an 850 nm laser diode, the pixel size of SLM 110 may be 850 nm. The pixel size influences the angular spread of a hologram since the angular spread is given by the Grating Equation:

$$\sin(\theta)=m\lambda/d \quad \text{(Equation 1)}$$

where θ is the angular spread of light, m is an integer number and the order of diffraction, and d is the distance of two pixels (a period). Hence, smaller pixel size generally yields more design freedom for generating holographic beams, although pixels sizes that are greater than the wavelength of light can also be used to generate holographic imaging signals. Display pixel array 113 may include square pixels (rather than the rectangular pixels in conventional RGB LCDs) so that the Grating Equation is applicable in both the row dimension and column dimension of the display pixel array 113.

In the illustrated embodiment, processing logic 101 selectively activates infrared emitter 105 and infrared light director 106 directs the infrared light to illuminate display pixel array 113 as infrared wavefront 107 while the holographic pattern is driven onto array 113. Infrared wavefront 107 is the same wavelength as infrared reference wavefront 157. Processing logic 101 may deactivate reference wavefront generator 155 while display pixel array 113 is being illuminated by infrared wavefront 107. Processing logic 101 may be configured to drive the reference wavefront generator 155 to emit the infrared reference wavefront 157 and initiate the infrared image capture by the image pixel array 170 while the reference wavefront generator 155 and the infrared illuminator 151 are emitting the infrared reference wavefront 157 and the general illumination emission 152, respectively.

Display pixel array 113 generates an infrared holographic imaging signal when the holographic pattern is illuminated by infrared wavefront 107 and the infrared holographic imaging signal is redirected by beam splitter 153 to exit system 100 as a reconstruction 144 (in reverse) of the shifted signal 143 that entered system 100. Reconstructed signal 144 follows (in reverse) whatever scattered path that shifted signal 143 took from voxel 133 to beam splitter 153 so reconstructed signal 144 is essentially "focused" back onto voxel 133.

Voxel 133 may absorb or scatter reconstructed signal 144 according to biological and/or optical characteristics of voxel 133 and sensors may measure an exit signal 145 of the reconstructed signal 144 that encounters voxel 133. System 100 may optionally include a sensor 190 coupled to processing logic 101 via an input/output X9 to initiate light measurement of exit signal 145 and pass the light measurement to processing logic 101. Although exit signal 145 is illustrated as being directed to sensor 190, the illustrated exit signal 145 is only a portion of the exit signal 145 that will be generated from signal 144 encountering voxel 133 and exit signal 145 will have many exit points from diffuse medium in addition to the illustrated portion of exit signal 145. The sensors that measure this exit signal may simply measure the amplitude of the exit signal. Sensor 190 may be a photodiode or a CMOS image sensor, for example. In one embodiment, the image pixel array 170 is used to measure the amplitude and/or phase of exit signal 145. The amplitude and/or phase of the exit signal 145 may be used to generate an image of diffuse medium 130. A reconstructed signal 144 may be directed to voxel 133 multiple times (with multiple corresponding measurements of exit signal 145) so that biological changes in voxel 133 may be recorded over a time range.

System 100 may refocus directional ultrasonic emitter 115 to different voxels of diffuse medium 130 and repeat the processes disclosed herein to raster scan diffuse medium 130 in order to generate a three-dimensional image of diffuse medium 130. Driving different holographic patterns onto display pixel array gives display pixel array 113 the ability to generate steerable holographic infrared beams that can focus an infrared signal (e.g. 144) to different voxels in three-dimensional space to facilitate the raster scanning of diffuse medium 130.

In one embodiment, processing logic 101 is configured to drive the reference wavefront generator 155 to emit the infrared reference wavefront 157 and initiate the infrared image capture by the image pixel array 170 while the reference wavefront generator 155 and the infrared illuminator 151 are emitting the infrared reference wavefront 157 and the general illumination emission 152, respectively.

Figure 2A:
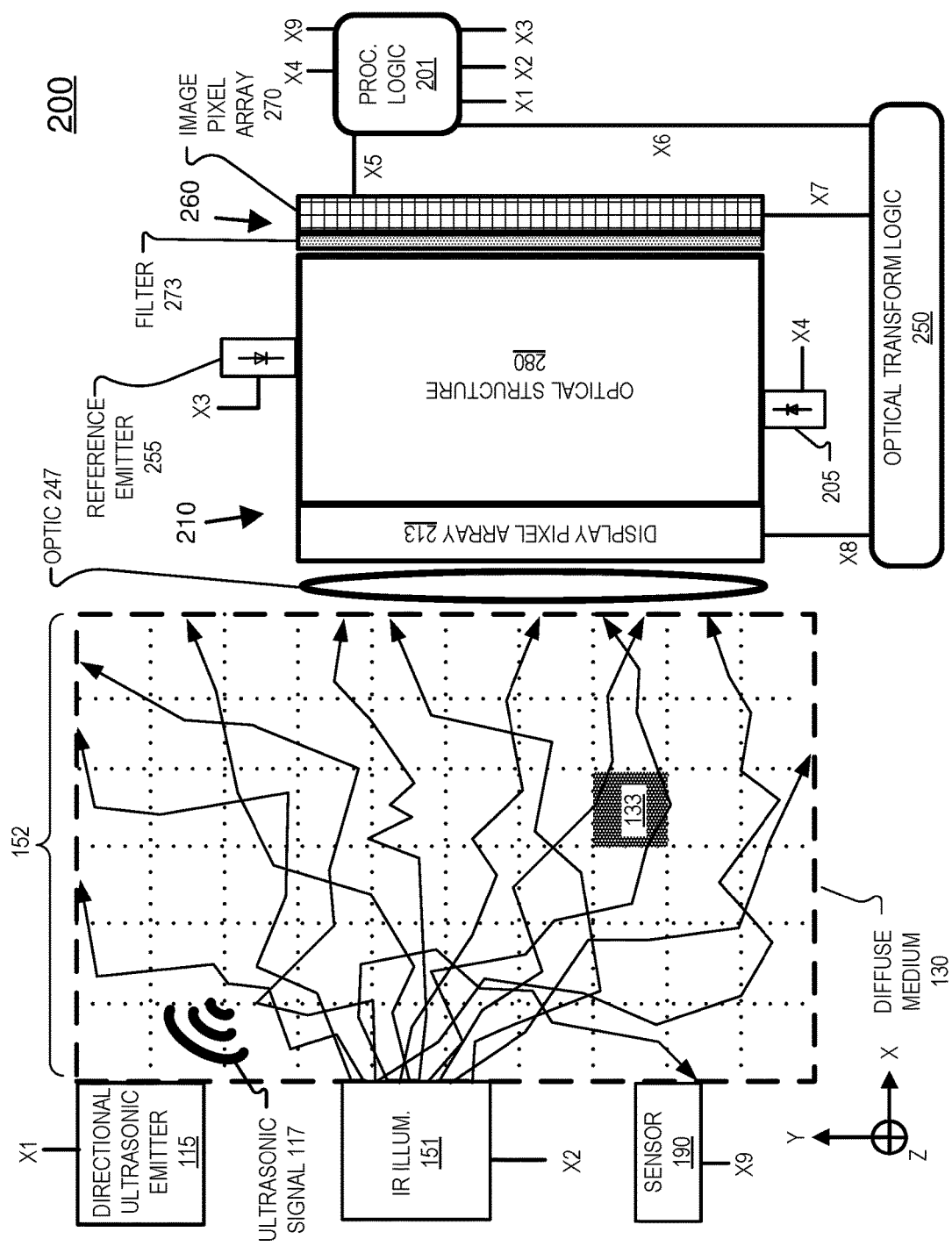
FIGS. 2A-2C illustrate an example imaging system that includes an image pixel array receiving an exit signal through a display pixel array, in accordance with an embodiment of the disclosure.
Figure 2B:
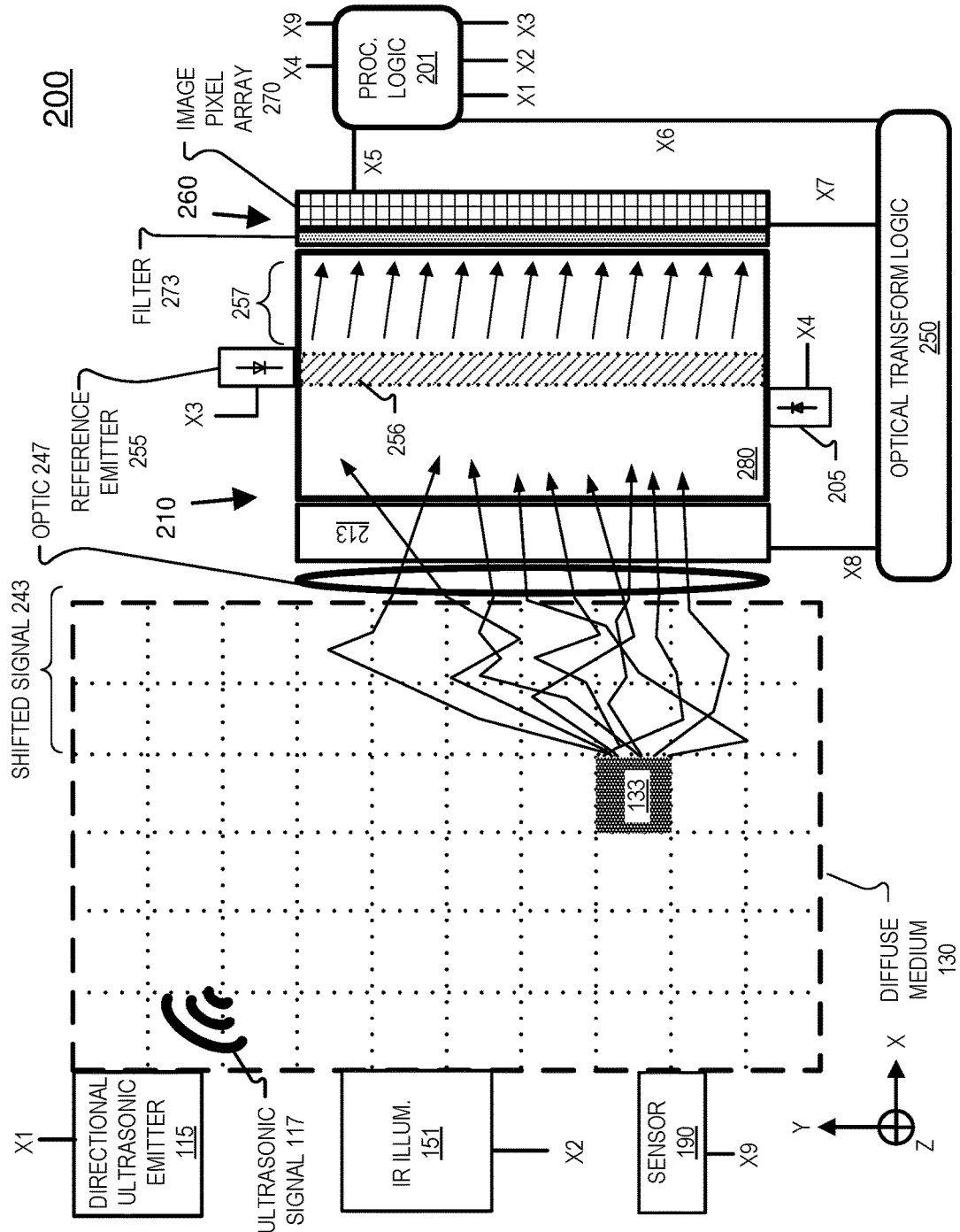
Figure 2C:
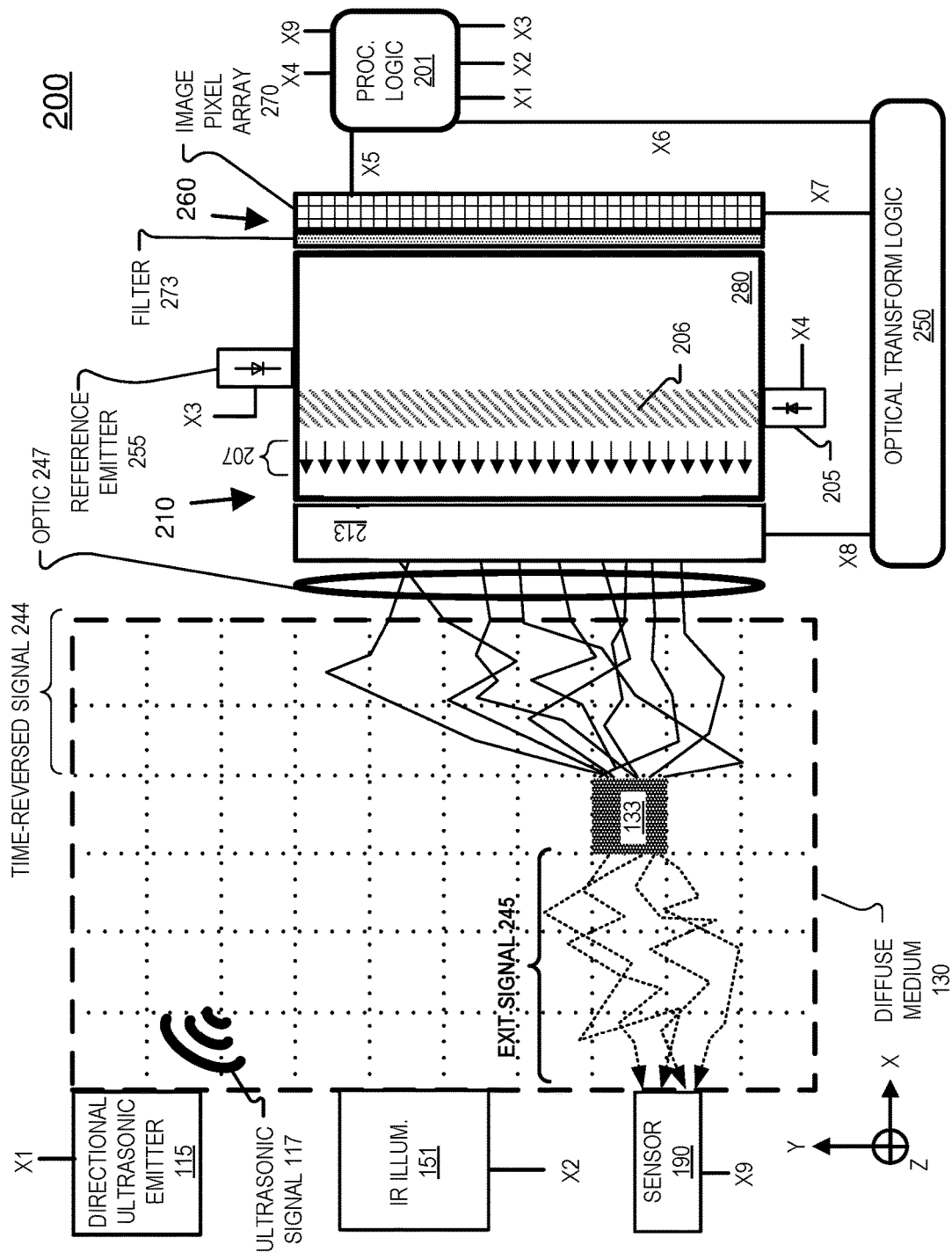

FIGS. 2A-2C illustrate an example imaging system 200 that includes an optical structure disposed between a display pixel array and an image pixel array, in accordance with an embodiment of the disclosure. System 200 illustrated in FIGS. 2A-2C functions similarly to system 100 of FIGS. 1A-1C although there are differences associated with the different positioning of the SLM 210, the imaging module 260, and the addition of optical structure 280.

Similarly to FIG. 1A, in FIG. 2A, processing logic 201 is coupled to drive directional ultrasonic emitter 115 to focus ultrasonic signal 117 to different locations in three-dimensional space, via output X1. Processing logic 201 is also coupled to selectively activate IR illuminator 151 via output X2, in the illustrated embodiment. System 200 may include a plurality of discrete devices that incorporate components of system 200, in some embodiments.

Imaging module 260 includes image pixel array 270 and filter(s) 273. In FIG. 2A, imaging system 200 also includes a directional ultrasonic emitter 115 coupled to be driven by processing logic 201. SLM 210 includes an infrared emitter 205, an infrared light director 206 (illustrated in FIG. 2C), and a display pixel array 213. Display pixel array 213 is a transmissive pixel array, in FIG. 2A.

Processing logic 201 may include a processor, microprocessor, cluster of processing cores, FPGA (field programmable gate array), and/or other suitable combination of logic hardware. In some embodiments, memories (not illustrated) are integrated into the processing logic to store instructions to execute operations and/or store data. An external memory or memories (not illustrated) may also be coupled to processing logic 201 to store instructions to execute operations and/or store data. A "memory" or "memories" described in this disclosure may include volatile or non-volatile memory architectures.

With ultrasonic signal 117 focused on voxel 133 in diffuse medium 130, IR illuminator 151 is selectively activated to emit general illumination emission 152 and a portion of emission 152 encounters voxel 133.

In FIG. 2B, the wavelength-shifted portion of the general illumination emission 152 is illustrated as shifted infrared imaging signal 243. Being influenced by ultrasonic signal 117, shifted infrared imaging signal 243 has a different wavelength (lambda-two) than general illumination emission 152 (lambda-one).

System 200 receives (at least a portion of) shifted signal 243. An input optic 247 may optionally be included in system 200. Input optic 247 may receive shifted signal 243 and focus the shifted signal 243 to be incident on image pixel array 270. In one embodiment, input optic 247 is configured to filter out an angled portion of the shifted signal 243, as described with regard to an embodiment of input optic 147.

Still referring to FIG. 2B, reference emitter 255 is configured to selectively emit an infrared reference light having the lambda-two wavelength so that infrared reference wavefront 257 interferes with the incoming shifted signal 243. Reference emitter 255 may include one or more laser diodes and reference director optic 256 in optical structure 280 may direct the lambda-two infrared reference light to image pixel array 270 as a substantially uniform infrared reference wavefront 257. Processing logic 201 is coupled to selectively activate reference emitter 255 via output X3, in the illustrated embodiment.

A linear polarizer may be included in system 200 to polarize shifted signal 243 to have the same polarization orientation as infrared reference wavefront 257. Reference emitter 255 may generate linear polarized light which imparts a polarization orientation to infrared reference wavefront 257. The linear polarizer may be included in optic 247, filter 273, or optical structure 280.

Shifted signal 243 may encounter input optic 247, display pixel array 213, and optical structure 280 prior to becoming incident upon image pixel array 270. The shifted signal 243 interferes with infrared reference wavefront 257 and image pixel array 270 captures an infrared image of the interference between shifted signal 243 and infrared reference wavefront 257. To allow shifted signal 243 to pass through display pixel array 213, each of the display pixels of the display pixel array 213 may be driven to a transmissive state while IR illuminator 151 and reference emitter 255 are activated.

In one embodiment, reference director optic 256 is configured to deliver the infrared reference wavefront 257 to the image pixel array 270 at an angle to a pixel plane of the image pixel array 270. Processing logic 201 is coupled to initiate the image capture by image pixel array 270 via output X5, in the illustrated embodiment.

In the illustrated embodiment, an infrared filter 273 is disposed between optical structure 280 and image pixel array 270. Infrared filter 273 may include the same configuration as infrared filter 173. Image pixel array 270 may include the same configuration as image pixel array 170. Image pixel array 270 is communicatively coupled to optical transform logic 250 to send the captured infrared image(s) to optical transform logic 250 for further processing. Optical transform logic 250 is coupled to image pixel array 270 via communication channel X7, in the illustrated embodiment. Optical transform logic 250 is coupled to receive the captured infrared image from the image pixel array 270 and provide a holographic pattern to be driven onto the display pixel array 213. The optical transform logic 250 is configured to extract phase data of the interference captured by the infrared image and the holographic pattern is generated from the phase data.

Referring now to FIG. 2C, display pixel array 213 is configured to generate an infrared holographic imaging signal 244 according to a holographic pattern driven onto the array 213. Optical transform logic 250 is coupled to provide the array 213 the holographic pattern to array 213 via communication channel X8.

In FIG. 2C, display pixel array 213 is illustrated as a transmissive LCD that is illuminated by infrared wavefront 207. In the illustrated embodiment, infrared emitter 205 is coupled to be driven by output X4 of processing logic 201. When processing logic 201 turns on (activates) IR emitter 205, infrared light propagates into IR light director 206. IR light director 206 redirects the infrared light toward display pixel array 213. IR emitter 205 is an infrared laser diode that emits monochromatic infrared light, in one embodiment.

In the illustrated embodiment, processing logic 201 selectively activates infrared emitter 205 and infrared light director 206 directs the infrared light to illuminate display pixel array 213 as infrared wavefront 207 while the holographic pattern is driven onto array 213. Infrared wavefront 207 is the same wavelength as infrared reference wavefront 257. Processing logic 201 may deactivate reference emitter 255 while display pixel array 213 is being illuminated by infrared wavefront 207. Processing logic 201 may be configured to drive the reference emitter 255 to emit the infrared reference wavefront 257 and initiate the infrared image capture by the image pixel array 270 while the reference emitter 255 and the infrared illuminator 151 are emitting the infrared reference wavefront 257 and the general illumination emission 152, respectively.

Display pixel array 213 generates an infrared holographic imaging signal 244 when the holographic pattern is illuminated by infrared wavefront 207 and the infrared holographic imaging signal 244 exits system 200 as a reconstruction (in reverse) of the shifted signal 243 that entered system 200. Reconstructed signal 244 follows (in reverse) whatever scattered path that shifted signal 243 took from voxel 133 to the display pixel array 213 so reconstructed signal 244 is essentially "focused" back onto voxel 133.

Voxel 133 may absorb or scatter reconstructed signal 244 according to biological characteristics of voxel 133 and sensors may measure an exit signal 245 of the reconstructed signal 244 that encounters voxel 133. System 200 may optionally include a sensor 190 coupled to processing logic 201 via an input/output X9 to initiate light measurement of exit signal 245 and pass the light measurement to processing logic 201. Although exit signal 245 is illustrated as being directed to sensor 190, the illustrated exit signal 245 is only a portion of the exit signal 245 that will be generated from signal 244 encountering voxel 133 and exit signal 245 will have many exit points from diffuse medium in addition to the illustrated portion of exit signal 245. The sensors that measure this exit signal may simply measure the amplitude of the exit signal. In one embodiment, the image pixel array 270 is used to measure the amplitude and/or phase of exit signal 245. The amplitude and/or phase of the exit signal 245 may be used to generate an image of diffuse medium 130. A reconstructed signal 244 may be directed to voxel 133 multiple times (with multiple corresponding measurements of exit signal 245) so that biological changes in voxel 133 may be recorded over a time range.

System 200 may refocus directional ultrasonic emitter 115 to different voxels of diffuse medium 130 and repeat the processes disclosed herein to raster scan diffuse medium 130 in order to generate a three-dimensional image of diffuse medium 130. Driving different holographic patterns onto display pixel array 213 gives display pixel array 213 the ability to generate steerable holographic infrared beams that can focus the reconstructed signal (e.g. 244) to different voxels in three-dimensional space to facilitate the raster scanning of diffuse medium 130.

In one embodiment, processing logic 201 is configured to drive the reference emitter 255 to emit the infrared reference wavefront 257 and initiate the infrared image capture by the image pixel array 270 while the reference emitter 255 and the infrared illuminator 151 are emitting the infrared reference wavefront 257 and the general illumination emission 152, respectively.

In system 200, image pixel array 270 is disposed in a parallel plane to display pixel array 213. However, in some embodiments, image pixel array 270 may be angled to increase the signal of interference between the infrared reference wavefront 257 and shifted signal 243. In system 100, image pixel array 170 is illustrated as being in a plane that is orthogonal to display pixel array 113. However, in some embodiment, image pixel array 170 may be angled to increase the isolation of the interference orders between the infrared reference wavefront 157 and shifted signal 143.

Although not specifically illustrated in FIGS. 1A-2C, infrared illuminator 151, reference wavefront generator 155 and infrared emitter 105 may be fiber optic outputs that are provided light via fiber optic from a single laser source. Similarly, infrared illuminator 151, reference emitter 255, and infrared emitter 205 may be provided light via fiber optic from a single laser source. The light from the single laser source may be modulated (e.g. by an acoustic optical modulator) to direct the laser light to the proper fiber optic for illumination. A micro-electro-mechanical system (MEMS) mirror, a digital micromirror device (DMD), or a mirror galvanometer may be used to selectively couple light from a single source into different fiber optic paths, in different embodiments. The light from the single laser source may also be selectively wavelength-shifted (e.g. by an acoustic optical modulator) to provide IR illuminator 151 with lambda-one wavelength light and to provide reference elements 105, 205, 155, and 255 with lambda-two wavelength light.

Figure 3:
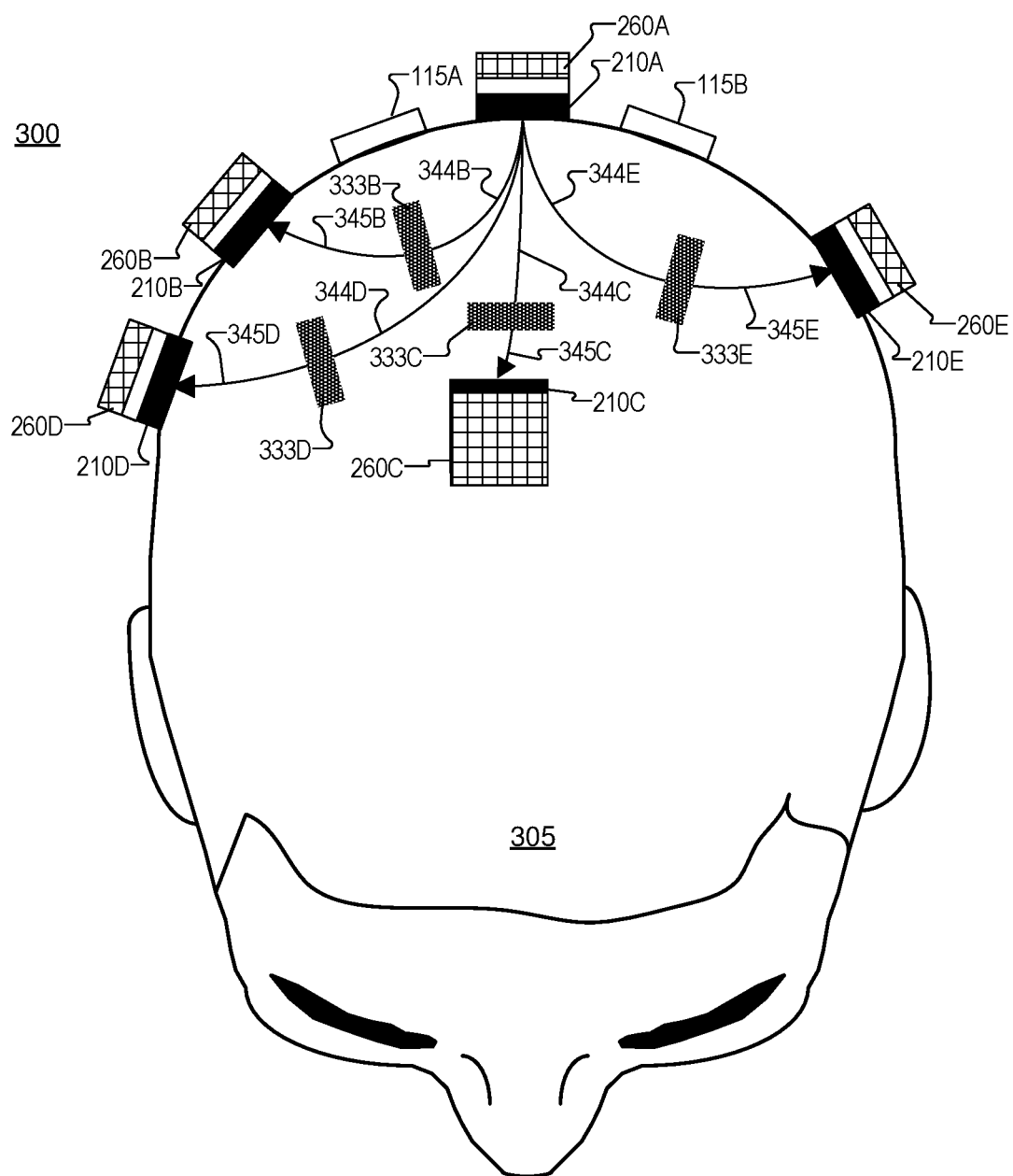
FIG. 3 illustrates an example placement of components of an imaging system in relationship to a human head, in accordance with an embodiment of the disclosure.

FIG. 3 illustrates an example placement of components of an imaging system 300 in relationship to a human head, in accordance with an embodiment of the disclosure. FIG. 3 is a top-down view of a human head 305. Imaging system 300 includes SLMs 210A-210E and imaging modules 260A-260E arranged as in system 200, and directional ultrasonic emitters 115A and 115B. Of course, SLMs 110 and imaging modules 160 may also be used instead of SLMs 210 and imaging modules 260 in imaging system 300. FIG. 3 shows that SLM 210A may generate multiple reconstructed infrared signals 344 that are directed to image different voxels 333 of the brain while the exit signals 345 are imaged by different imaging modules 260. The other SLMs 210B-210E may also generate reconstructed infrared signals 344 (not illustrated) directed to voxels where the exit signals are imaged by each of imaging modules 260A-E. Scientific literature suggests that the penetration depth of infrared light into tissue is around 10 cm so multiple SLMs 210 and imaging modules 160 may be needed to image the entire brain or other tissue. Although not illustrated, sensors 190 may also be placed around a diffuse medium such as human head 305 to measure the exit signals 345. A wearable hat may include system 300 so that system 300 can be worn as a wearable, in some embodiments. Other wearables may also include all or part of system 300.

Figure 4A:
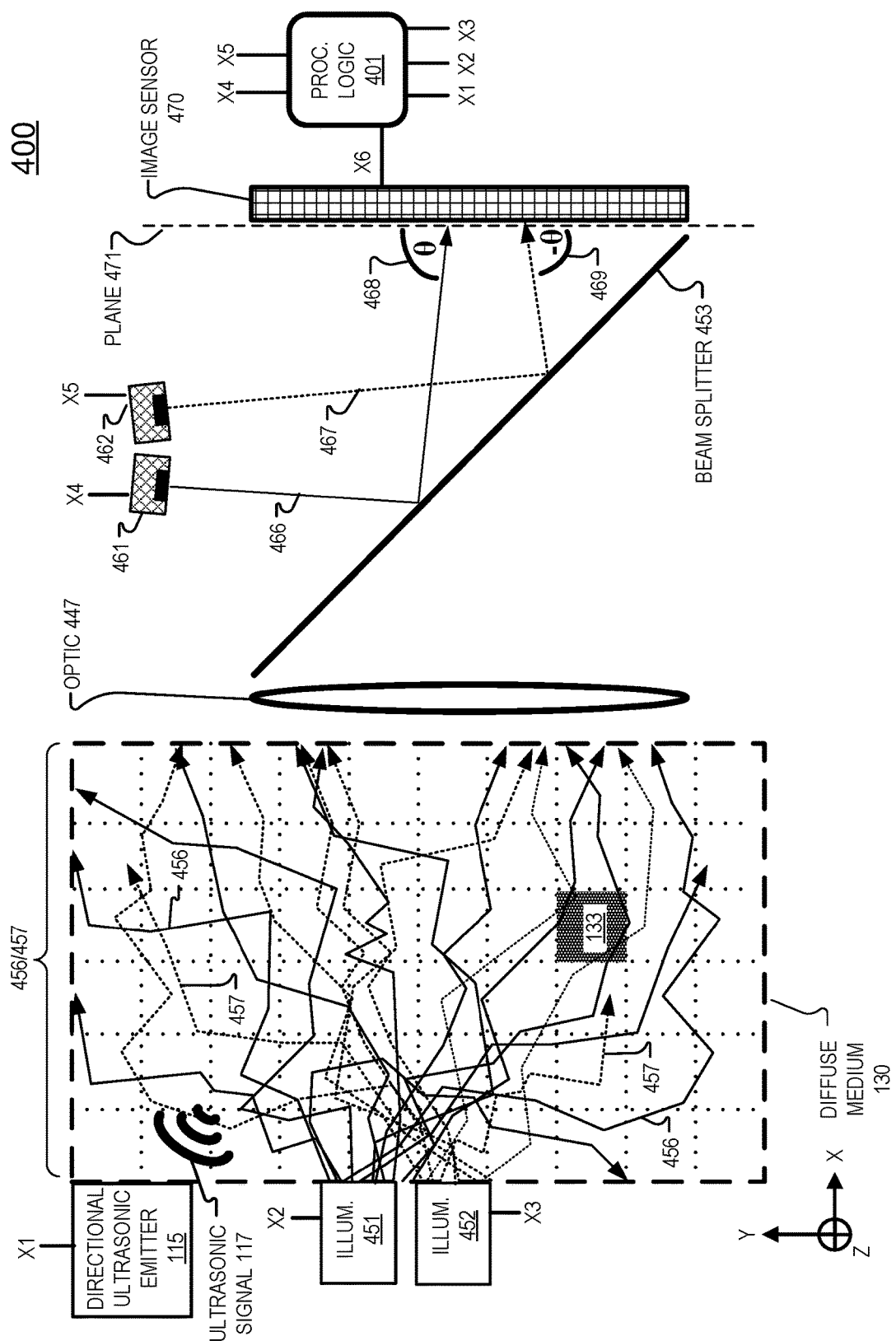
FIGS. 4A-4B illustrate an example dual-beam imaging system having two reference beam emitters, in accordance with an embodiment of the disclosure.

FIG. 4A illustrates an example dual-beam imaging system 400 that includes two illuminators and two reference emitters, in accordance with an embodiment of the disclosure. System 400 includes image sensor 470, beam splitter 453, optic 447, and processing logic 401. Image sensor 470 may include a two-dimensional image pixel array arranged in rows and columns that define a pixel plane of the image sensor 470. Image sensor 470 may be a CMOS image sensor in some embodiments. Image sensor 470 may include an image pixel array similar to image pixel array 170, in some embodiments.

Processing logic 401 may include a processor, microprocessor, cluster of processing cores, FPGA (field programmable gate array), and/or other suitable combination of logic hardware. In some embodiments, memories (not illustrated) are integrated into the processing logic to store instructions to execute operations and/or store data. An external memory or memories (not illustrated) may also be coupled to processing logic 401 to store instructions to execute operations and/or store data. A "memory" or "memories" described in this disclosure may include volatile or non-volatile memory architectures.

System 400 includes a first illuminator 451 configured to emit a first illumination beam 456 illustrated with solid lines, in FIG. 4A. System 400 also includes a second illuminator 452 configured to emit a second illumination beam 457 illustrated with dotted lines, in FIG. 4A. First illumination beam 456 is a first wavelength that is different than a second wavelength of second illumination beam 457. In one embodiment, first illumination beam 456 is centered around 600 nm. Second illumination beam 457 may be centered around 800 nm. First illumination beam 456 and second illumination beam 457 may both be centered around near-infrared wavelengths, in some embodiments. Processing logic 401 is coupled to selectively activate first illuminator 451 via output X2, in the illustrated embodiment. First illuminator 451 may include a laser generating first illumination beam 456. Processing logic 401 is coupled to selectively activate second illuminator 452 via output X3, in the illustrated embodiment. Second illuminator 452 may include a laser generating second illumination beam 457. Of course, a laser may generate monochromatic coherent light. Monochromatic light may be defined as light within a 4 nm frequency band, for example. First illuminator 451 and/or second illuminator 452 may include a fiber optic coupled to a light source to provide the illumination beam into diffuse medium 130.

Illuminator 451 and 452 are disposed to direct the first illumination beam 456 and second illumination beam 457 into the diffuse medium 130. In the context of imaging tissue, beams 456 and 457 will be significantly scattered within tissue within as little as 1 cm of depth into the tissue when tissue is the diffuse medium 130. At least a portion of beams 456 and 457 will encounter voxel 133, as illustrated in FIG. 1A.

System 400 also includes ultrasonic emitter 115. Ultrasonic emitter 115 is configured to focus an ultrasonic signal 117 to a point in three-dimensional space. In the medical context, the ultrasonic emitter 115 is configured to focus an ultrasonic signal 117 to a voxel within the human body. The voxel may be within the brain, abdomen, or uterus, for example. Processing logic 401 is coupled to drive directional ultrasonic emitter 115 to focus ultrasonic signal 117 to different locations in three-dimensional space via output X1, in the illustrated embodiment. The directional ultrasonic emitter 115 can be driven to focus an ultrasonic signal to voxel 133 in three-dimensional diffuse medium 130, for example. Focusing an ultrasonic signal 117 to a given voxel of tissue (e.g. voxel 133) influences the portion of beams 456 and 457 that encounters the voxel by wavelength-shifting that portion of beams 456 and 457 that propagates through that voxel.

Figure 4B:
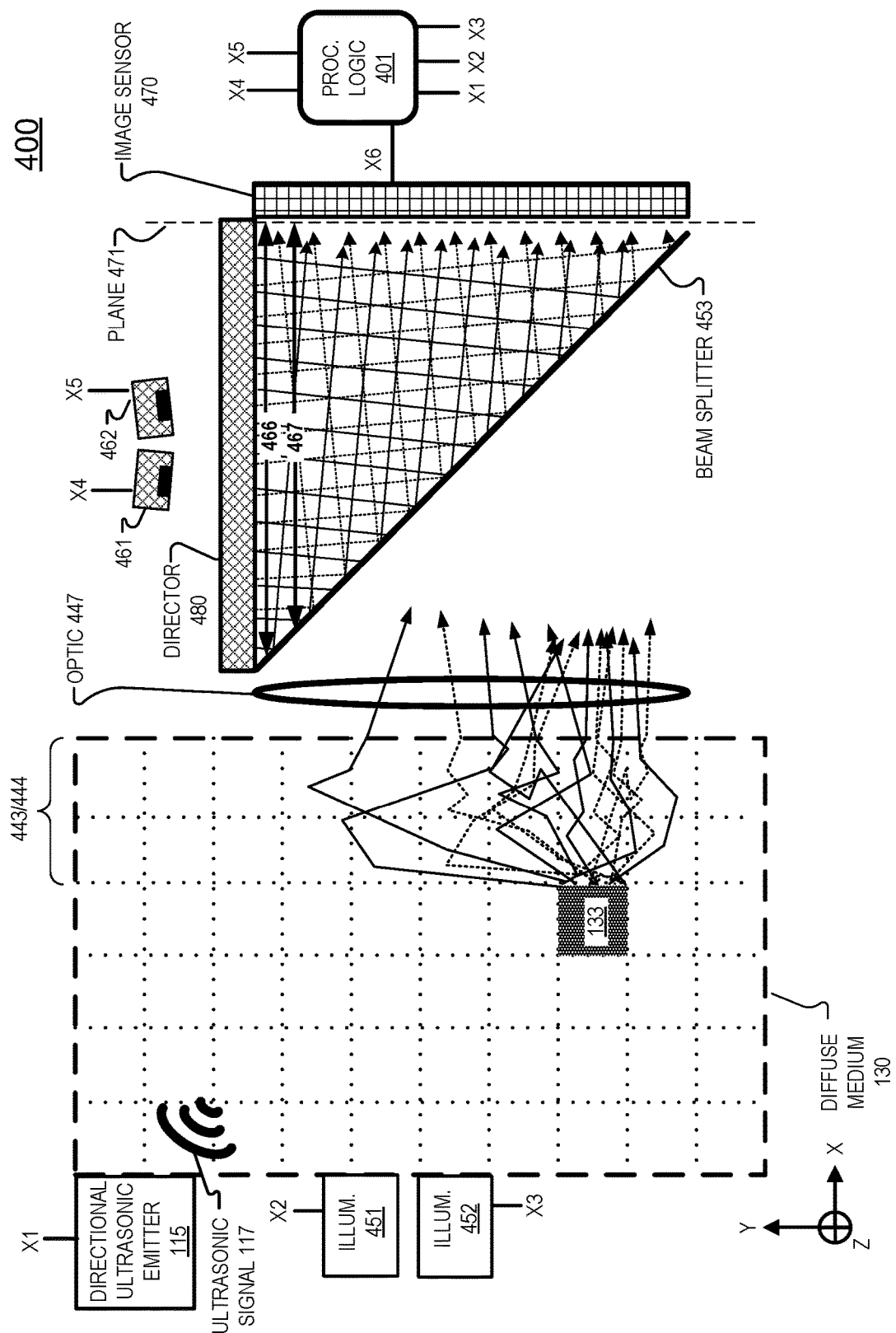

In FIG. 4B, the wavelength-shifted portion of the first illumination beam 456 is illustrated as first wavelength-shifted exit signal 443 and the wavelength-shifted portion of the second illumination beam 457 is illustrated as second wavelength-shifted exit signal 444. Being influenced by ultrasonic signal 117, wavelength-shifted exit signals 443/444 have slightly different wavelengths than illumination beams 456/457. In some embodiments, the delta between signal 456 and 443 is less than 1 nanometer. In an embodiment, the delta between signal 456 and 443 is less than 20 femtometer. In some embodiments, the delta between signal 457 and 444 is less than 1 nanometer. In an embodiment, the delta between signal 457 and 444 is less than 20 femtometer.

System 400 receives (at least a portion of) wavelength-shifted exit signals 443/444. An input optic 447 may optionally be included in system 400. Input optic 447 may receive signal 443/444 and direct signals 443/444 to be incident on image sensor 470. In one embodiment, input optic 447 is configured to filter out an angled portion of signals 443/444 that is above an angle acceptance threshold. In one embodiment, a controlled aperture is included in input optic 447 to restrict the angle of incident signals 443/444 receiving into system 400. Filtering out extreme angles of signals 443/444 may provide for improved imaging of the interference patterns. A linear polarizer may be included in system 400 to polarize signals 443/444 to have the same polarization orientation reference beams 466/467. The linear polarizer may be disposed on or within the input optic 447, in some embodiments.

System 400 includes a first reference emitter 461 and a second reference emitter 462. Processing logic 401 is coupled to drive first reference emitter 461 via communication channel X4 to emit first reference beam 466 and coupled to drive second reference emitter 462 via communication channel X5 to emit second reference beam 467. First reference beam 466 is the same wavelength as the first wavelength-shifted exit signal 443 and second reference beam 467 is the same wavelength as the second wavelength-shifted exit signal 444. First reference emitter 461 may include a laser, laser diode, and/or a fiber optic coupled to a light source to provide reference beam 466. Second reference emitter 462 may include a laser, laser diode, and/or a fiber optic coupled to a light source to provide reference beam 467.

FIG. 4A illustrates a single ray of first reference beam 466 and second reference beam 467 to illustrate that first reference beam 466 is received by image sensor 470 at a first reference angle 468 with respect to the pixel plane 471 of image sensor 470 and that second reference beam 467 is received by image sensor 470 at a second reference angle 469 with respect to the pixel plane 471 of image sensor 470. In the illustrated embodiment of FIG. 4A, first reference angle 468 is θ and second reference angle 469 is −θ. In one embodiment, first reference angle 468 is 83 degrees and second reference angle is −83 degrees. The pixel plane 471 may be defined as the plane formed by the two-dimensional array of image pixels of image sensor 470 that are arranged in rows and columns.

Beam splitter 453 direct rays from first reference emitter 461 and second reference emitter 462 to image sensor 470. First reference emitter 461 and second reference emitter 462 are angled so that the first reference beam 466 and second reference beam are incident at their opposite angles 468 and 469. Beam splitter 453 may be a 50/50 reflective layer that passes 50% of light and reflects 50% of light. In some embodiments, beam splitter 453 is less than 30% reflective. Beam splitter 453 may be a partially reflective layer that passes 80% of light and reflects 20% of light. Beam splitter 453 may be a partially reflective layer that passes 90% of light and reflects 10% of light. Beam splitter 453 may be a partially reflective layer that passes 95% of light and reflects 5% of light.

Referring again to FIG. 4B, signal 443 encounters beam splitter 453 and a first portion of signal 443 passes through beam splitter 453 while the remaining portion of signal 443 is reflected by beam splitter 453. The first portion of the shifted signal 443 that passes through beam splitter 453 interferes with the first portion of first reference beam 466 that is redirected to image sensor 470 and image sensor 470 captures the interference between signal 443 and first reference beam 466 as a first interference pattern. Signal 444 also encounters beam splitter 453 and a first portion of signal 444 passes through beam splitter 453 while the remaining portion of signal 444 is reflected by beam splitter 453. The first portion of the shifted signal 444 that passes through beam splitter 453 interferes with the first portion of second reference beam 467 that is redirected to image sensor 470 and image sensor 470 captures the interference between signal 444 and first reference beam 467 as a second interference pattern. Processing logic 401 is communicatively coupled to image sensor 470 via communication channel X6 and the image that includes the first interference pattern and second interference pattern may be provided to processing logic 401 by way of communication channel X6. Processing logic 401 may be configured to initiate an image capture while driving the first reference emitter 461 and the second reference emitter 462 to emit the first reference beam 466 and second reference beam 467. Illuminators 451 and 452 may also be driven to emit illumination beams 456/457 while image sensor is capturing the image. Processing logic 401 may transmit an image capture signal via communication channel X6 to initiate the image capture. Image sensor 470 may initiate a global electronic shutter or a rolling electronic shutter to capture the image in response to receiving the image capture signal.

FIG. 4B shows that light director 480 may distribute first reference beam 466 across beam splitter 453 and consequently across image sensor 470. FIG. 4B shows that light director 480 may distribute second reference beam 467 across beam splitter 453 and consequently across image sensor 470. Light director 480 may be a waveguide or waveguides that first reference emitter 461 and second reference emitter 462 illuminate with their respective reference beams for a more even distribution to beam splitter 453.

In FIG. 4B, the distributed first reference beam 466 is illustrated as solid lines and distributed reference beam 467 is illustrated as dotted lines that are angle offset from distributed reference beam 466 so that, after reflection from beam splitter 453, reference beams 466 and 467 are incident upon image sensor 470 at their engineered reference angles. Interfering first reference beam 466 with the first wavelength-shifted exit signal 443 at a first reference angle and interfering second reference beam 467 with the second wavelength-shifted exit signal 444 at a second reference angle that is different from the first reference angle separates the first interference pattern and second interference pattern in Fourier space (frequency domain) of the image captured by image sensor 470. Consequently, in a single image capture, the first interference pattern and the second interference pattern can be captured simultaneously and the absorption of voxel 133 for different wavelengths of light is therefore captured in the same time period. Although the interference of signal 443 and 466 is not specifically illustrated, it is understood by those skilled in the art that first reference beam 466 is illuminating beam splitter 453 at the same time that signal 443 passes through beam splitter 453 to interfere with first reference beam 466. Similarly, second reference beam 467 is illuminating beam splitter 453 at the same time that signal 444 passes through beam splitter 453 to interfere with second reference beam 467.

The components of system 400 may be included in a single imaging device. Or, the components of system 400 may be included in multiple devices that are in communication with each other. Multiple components of system 400 may be arranged similarly to the imaging components in FIG. 3 to increase the imaging are capabilities of system 400.

Figure 5:
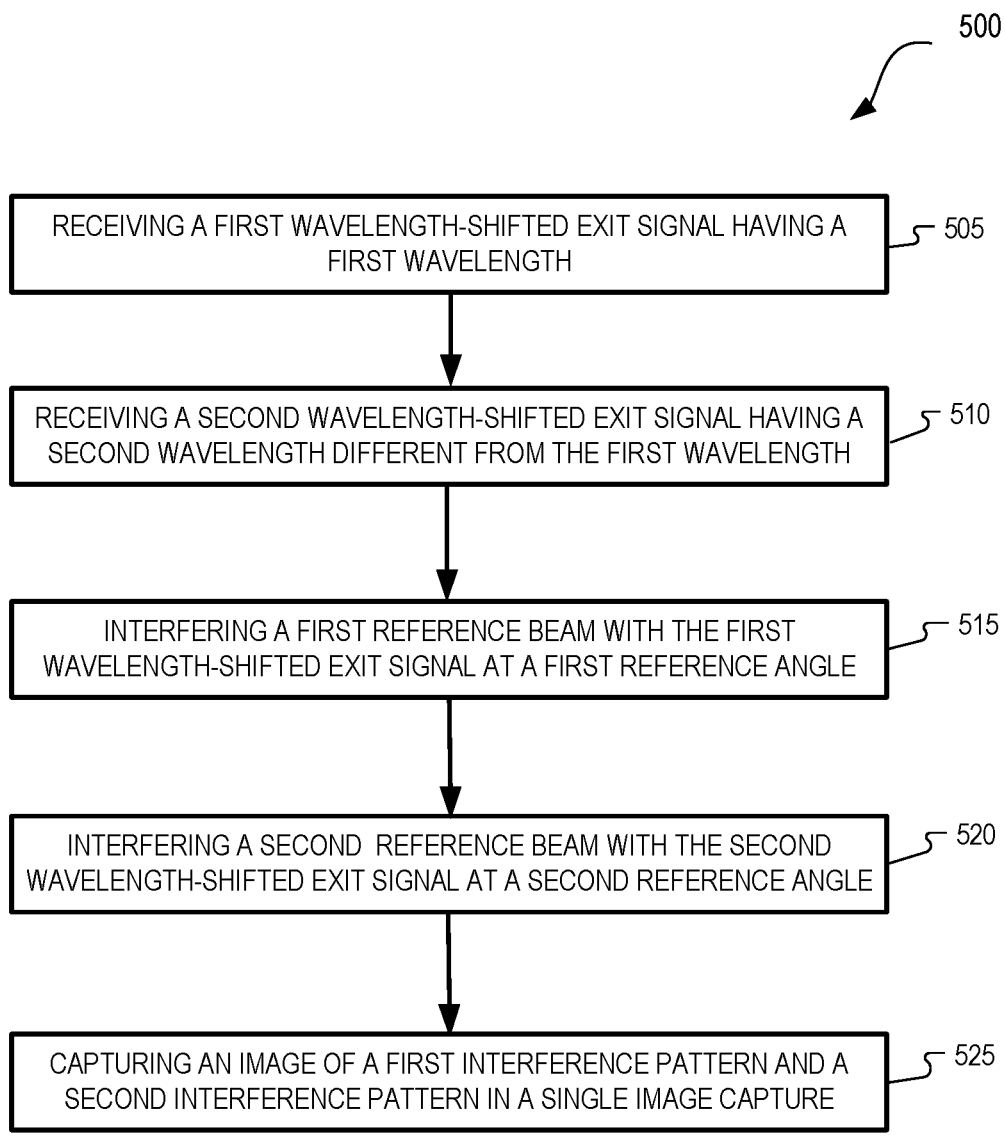
FIG. 5 illustrates an example flow chart of a process of dual-beam imaging, in accordance with an embodiment of the disclosure.

FIG. 5 illustrates an example flow chart of a process 500 of dual-beam imaging, in accordance with an embodiment of the disclosure. The order in which some or all of the process blocks appear in process 500 should not be deemed limiting. Rather, one of ordinary skill in the art having the benefit of the present disclosure will understand that some of the process blocks may be executed in a variety of orders not illustrated, or even in parallel. Processing logic 401 may execute the operations of process 500, for example.

In process block 505, a first wavelength-shifted exit signal (e.g. 456) is received from a medium (e.g. 130). The first wavelength-shifted exit signal has a first wavelength (e.g. 600 nm). The first wavelength-shifted exit signal may have a very narrow band.

In process block 510, a second wavelength-shifted exit signal (e.g. 457) is received from the medium. The second wavelength-shifted exit signal has a second wavelength (e.g. 800 nm) that is different than the first wavelength. The second wavelength-shifted exit signal may have a very narrow band.

In process block 515, a first reference beam (e.g. 466) is interfered with the first wavelength-shifted exit signal at a first reference angle (e.g. angle 468).

In process block 520, a second reference beam (e.g. 467) is interfered with the second wavelength-shifted exit signal at a second reference angle (e.g. angle 469). The first reference beam is of the first wavelength and the second reference beam is of the second wavelength.

In process block 525, an image is captured in a single image capture of an image sensor that includes a first interference pattern and a second interference pattern. The first interference pattern is generated by the first reference beam interfering with the first wavelength-shifted exit signal. The second interference pattern is generated by the second reference beam interfering with the second wavelength-shifted exit signal.

In one embodiment, the first reference angle is $\theta$ with respect to a pixel plane (e.g. 471) of the image sensor and the second reference angle is $-\theta$ with respect to the pixel plane of the image sensor. Prior to receiving the first and second wavelength-shifted exit signals, process 500 may further include illuminating the medium with a first illumination beam (e.g. 456) and illuminating the medium with a second illumination beam (e.g. 457). Process 500 may further include directing an ultrasonic signal (e.g. 117) to a voxel of the medium to wavelength-shift the first illumination beam into the first wavelength-shifted exit signal and to wavelength-shift the second illumination beam into the second wavelength-shifted exit signal.

After capturing the image in process block 525, in some embodiments, process 500 may further include generating a frequency domain image by performing a Fourier transform operation on the image that includes the first interference pattern and the second interference pattern. A first portion of the frequency domain image is compared with a second portion of the frequency domain image. A first intensity of the first portion of the frequency domain image is associated with the first interference pattern and a second intensity of the second portion of the frequency domain image is associated with the second interference pattern. A difference value is generated in response to comparing the first portion and the second portion. In one embodiment, a blood oxygenation level is generated based at least in part on the difference value.

Figure 6:
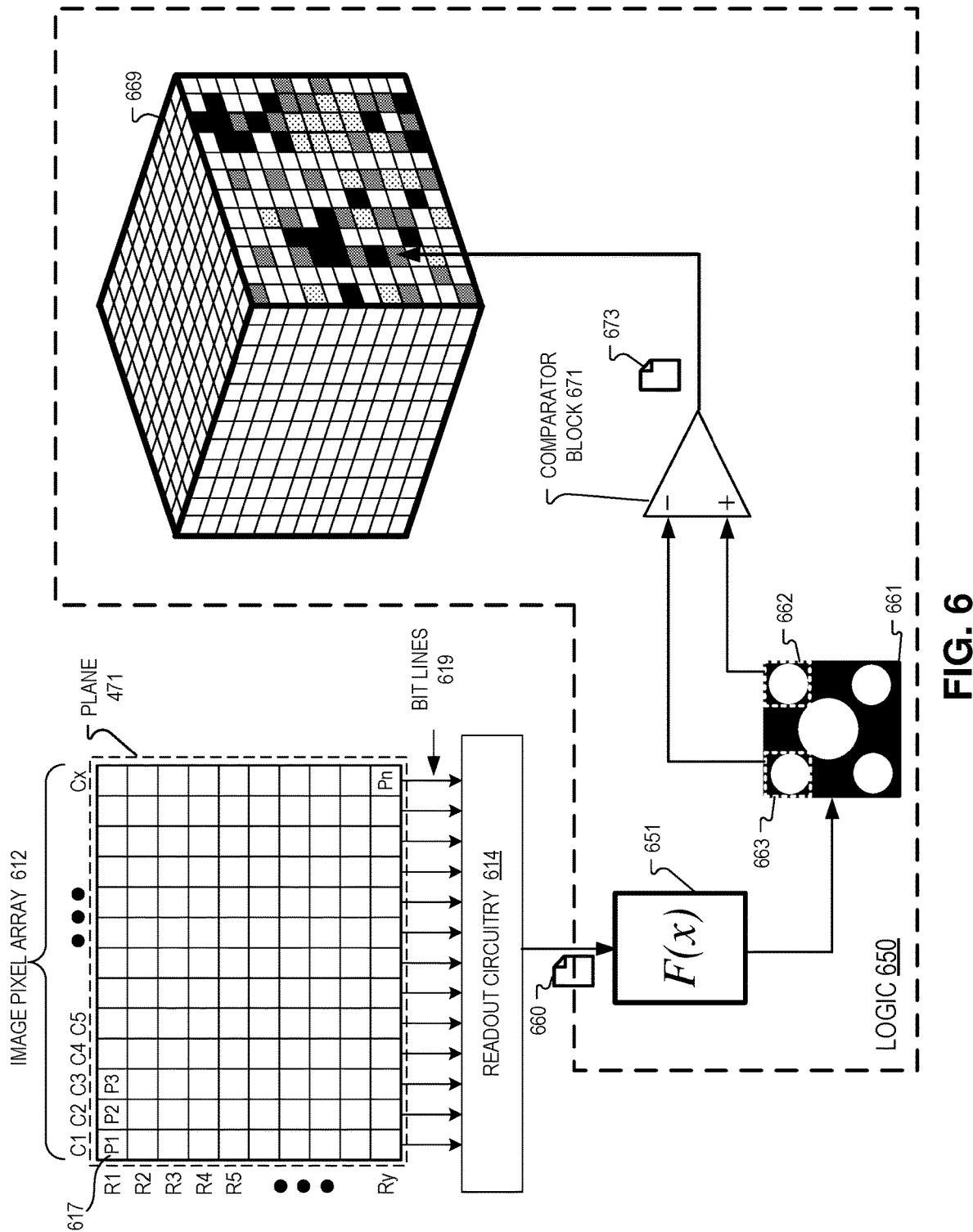
FIG. 6 illustrates an example image pixel array coupled to example extraction logic, in accordance with an embodiment of the disclosure.

FIG. 6 illustrates an image pixel array 612 coupled to example extraction logic 650, in accordance with an embodiment of the disclosure. Image pixel array 612 includes image pixels 617 arranged in integer number×columns and integer number y rows. Readout circuitry 614 is coupled to read the signal value from each image pixel 617 via bitlines 619. Image pixel array 612, readout circuitry 614, and bitlines 619 may be included in image sensor 470 of FIG. 4, for example. Fourier transform engine 651 in extraction logic 650 is coupled to receive the captured image 660 from readout circuitry 614, in FIG. 6. Image 660 includes both the first interference pattern and the second interference pattern. Fourier transform engine 651 generates a frequency domain image 661 by performing a Fourier transform on image 660 received from readout circuitry 614.

Frequency domain image 661 includes a first portion 662 and a second portion 663. The circle in the first portion 662 is representative of the intensity of the first interference pattern and the circle in the second portion 663 is representative of the intensity of the second interference pattern. The intensity circles are neatly distinguished in different corners of frequency domain image 661 due to the first reference angle 468 having the opposite orientation of second reference angle 469. Therefore, by having the reference angles of the reference beams be opposite orientations, the first interference pattern and the second interference pattern are more easily measured by the same image sensor in the same image capture.

In one embodiment, the circle in the first portion 662 represents a first order of interference between signal 443 and reference beam 466 and the circle in the second portion 663 represents a first order of interference between signal 444 and reference beam 467. The $0^{th}$ order and the −1 order may be filtered out of image 661 so that only the first orders remain. Since the differing wavelengths of signals 443 and 444 are aborbed differently by oxygenated and deoxygenated blood, the difference between the two "first orders" of the interferences can indicate the oxygenation level of a given voxel.

Comparator block 671 is coupled to receive the first portion 662 and the second portion 663 for comparing. In some embodiments, the intensity data associated with the intensity circles may be stripped from the first and second portions, respectively prior to comparing them. The intensity data of the circles may be stripped from the first and second portions using masks, for example. In one embodiment, the Fourier coefficients are extracted from the first portion 662 of image 661 and a sum of the squares of the absolute value of the Fourier coefficients is calculated. The sum of the squares is then used as intensity data of the first portion 662 that is provided to comparator block 671. In one embodiment, the Fourier coefficients are extracted from the second portion 663 of image 661 and a sum of the squares of the absolute value of the Fourier coefficients is calculated. The sum is then used as intensity data of the second portion 663 that is provided to comparator block 671. Difference value 673 is generated by comparator block 671. Difference value 673 may be derived from a difference between the intensity data from the first portion 662 and the intensity data from the second portion 663. Difference value 673 may represent an oxygenation level of blood flowing through voxel 133.

Extraction logic 650 incorporates the difference value 673 as a voxel value in a composite image 669. Composite image 669 is illustrated as a three-dimensional image in FIG. 6 and may be a three-dimensional image of a diffuse medium. As described in this disclosure, the system 400 may raster scan through diffuse medium 130 (focusing on different voxels) to generate a three-dimensional image of diffuse medium.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

Communication channels described in this disclosure may include wired or wireless communications utilizing IEEE 802.11 protocols, BlueTooth, SPI (Serial Peripheral Interface), I²C (Inter-Integrated Circuit), USB (Universal Serial Port), CAN (Controller Area Network), cellular data protocols (e.g. 3G, 4G, LTE, 5G), or otherwise The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method of imaging, the method comprising:
   receiving a first wavelength-shifted exit signal from a medium, wherein the first wavelength-shifted exit signal has a first wavelength;
   receiving a second wavelength-shifted exit signal from the medium, wherein the second wavelength-shifted exit signal has a second wavelength different from the first wavelength;
   interfering a first reference beam with the first wavelength-shifted exit signal at a first reference angle, wherein the first reference beam is the same wavelength as the first wavelength-shifted exit signal;
   interfering a second reference beam with the second wavelength-shifted exit signal at a second reference angle that is different from the first reference angle, wherein the second reference beam is the same wavelength as the second wavelength-shifted exit signal; and
   capturing an image of a first interference pattern of the first reference beam interfering with the first wavelength-shifted exit signal and a second interference pattern of the second reference beam interfering with the second wavelength-shifted exit signal, wherein the first interference pattern and the second interference pattern are captured in a single image capture of an image sensor.

2. The method of claim 1, wherein the first reference angle is $\theta$ with respect to a pixel plane of the image sensor, and wherein the second reference angle is $-\theta$ with respect to the pixel plane of the image sensor.

3. The method of claim 1 further comprising:
   generating a frequency domain image by performing a Fourier transform operation on the image;
   comparing a first portion of the frequency domain image with a second portion of the frequency domain image, wherein a first intensity of the first portion of the frequency domain image is associated with the first interference pattern, and wherein a second intensity of the second portion of the frequency domain image is associated with the second interference pattern; and
   generating a difference value in response to the comparing the first portion and the second portion.

4. The method of claim 3, wherein the first portion of the frequency domain image is within a first corner of the frequency domain image, and wherein the second portion of the frequency domain image is within a second corner of the frequency domain image, the second corner adjacent to the first corner and the first corner not overlapping the second corner.

5. The method of claim 3 further comprising:
   generating a blood oxygenation level based at least in part on the difference value.

6. The method of claim 1 further comprising:
   illuminating the medium with a first illumination beam, wherein the first wavelength-shifted exit signal is a wavelength-shifted version of the first illumination beam; and
   illuminating the medium with a second illumination beam, wherein the second wavelength-shifted exit signal is a wavelength-shifted version of the second illumination beam.

7. The method of claim 6 further comprising:
   directing an ultrasonic signal to a voxel of the medium to wavelength-shift the first illumination beam into the first wavelength-shifted exit signal and to wavelength-shift the second illumination beam into the second wavelength-shifted exit signal.

8. The method of claim 1, wherein the first reference beam is a first coherent beam emitted from a laser, and wherein the second reference beam is a second coherent beam.

9. The method of claim 1, wherein the first wavelength is within a visible light spectrum, and wherein the second wavelength is within a near-infrared spectrum.

10. The method of claim 1, wherein the image sensor includes a CMOS image pixel array.

11. The method of claim 1, wherein the first wavelength-shifted exit signal is a wavelength-shifted version of a first laser illumination beam, and wherein the second wavelength-shifted exit signal is a wavelength-shifted version of a second laser illumination beam.

12. The method of claim 1, wherein the first laser illumination beam is monochromatic light and the second laser illumination beam is monochromatic light.

13. The method of claim 1, wherein the first reference angle is with respect to a pixel plane of the image sensor, and wherein the second reference angle is with respect to the pixel plane of the image sensor.

14. The method of claim 1, wherein the first wavelength-shifted exit signal is visible light, and wherein the second wavelength-shifted exit signal is near-infrared light.

15. The method of claim 1, wherein a wavelength difference between the first wavelength-shifted exit signal and the second wavelength-shifted exit signal is approximately 200 nm.

\* \* \* \* \*